US006694197B1

(12) United States Patent
Hatcher et al.

(10) Patent No.: US 6,694,197 B1
(45) Date of Patent: Feb. 17, 2004

(54) SINGLE CHANNEL REFORMATTER

(75) Inventors: Thomas James Hatcher, Burlington Township, NJ (US); Aleksandr Grinberg, Old Bridge, NJ (US)

(73) Assignee: Pharmacopeia Drug Discovery Inc., Princeton, NJ (US)

( * ) Notice: Subject to any disclaimer, the term of this patent is extended or adjusted under 35 U.S.C. 154(b) by 0 days.

(21) Appl. No.: 09/556,537

(22) Filed: Apr. 24, 2000

(51) Int. Cl.[7] ............................................... G05B 19/18
(52) U.S. Cl. ............................ 700/56; 700/57; 700/60; 700/61; 700/83; 422/65; 422/100
(58) Field of Search ..................... 700/61, 56, 246, 700/18, 213, 218, 57, 60, 83, 275; 702/31; 422/100, 65, 63, 67, 103; 356/72; 436/43, 49, 54

(56) References Cited

U.S. PATENT DOCUMENTS

| 5,369,566 | A | * | 11/1994 | Pfost et al. | ................... 700/18 |
| 5,985,214 | A | * | 11/1999 | Stylli et al. | ................... 422/65 |
| 6,347,259 | B1 | * | 2/2002 | Goldenberg et al. | ......... 700/218 |
| 6,372,185 | B1 | * | 4/2002 | Shumate et al. | ............ 422/100 |
| 6,608,671 | B2 | * | 8/2003 | Tsien et al. | .................... 356/72 |

* cited by examiner

Primary Examiner—Leo Picard
Assistant Examiner—Steven R. Garland
(74) Attorney, Agent, or Firm—DeMont & Breyer LLC

(57) ABSTRACT

A single channel reformatter having a syringe that is movable along a z-axis by a z-positioner. A x-y positioner is capable of positioning any well of a source plate having a plurality of wells, and of positioning any well of a destination plate having a plurality of wells, beneath the syringe. Liquid from a well of the source plate is aspirated by the syringe and dispensed into one or more wells of the destination plate. Since the syringe does not move in the x-y plane, it is advantageously integrated into a wash system that cleanses it between liquid transfer operations. The drive element that actuates the syringe to aspirate and dispense during liquid transfer operations is advantageously used to drive the wash cycle. In a method according to present invention for controlling the reformatting operation, well-to-well links are specified, a preferred execution order for executing the specified links is determined, and the specified links are executed in the preferred order.

8 Claims, 13 Drawing Sheets

SINGLE CHANNEL REFORMATTER

FIELD OF THE INVENTION

The present invention relates to an article for handling small volumes of liquid. More particularly, the present invention relates to an article capable of transferring liquid, on a well-to-well basis, from a source container having a first format or configuration (e.g., a 96-well micro-titer plate, a vial, etc.) to a destination container having a second format (e.g., a 1536-well micro-titer plate).

BACKGROUND OF THE INVENTION

Advances in the field of combinatorial chemistry, high throughput screening and genomics research have pushed liquid handling capabilities of conventional devices and instrumentation to the limit with regard to high-speed handling of micro-volumes of liquid (i.e., from 0 to about 2 microliters). Specifically, many of the techniques used in such fields require aspirating liquid from and dispensing liquid into micro-titer plates or other containers configured to retain very small quantities of liquid.

Progress in the aforementioned fields is generating a need to miniaturize assay format from, for example, the common 96-well micro-titer plate (6.5 mm well diameter) to 384-well plates (3.5 mm square wells) and to state-of-the-art 1536-well plates (1.3 mm well diameter). With these and other assay formats in use, situations arise wherein liquid must be transferred between plates having different formats. The usual application is transferring liquid from a relatively lower density format, such as a 96-well plate, to a relatively higher density format, such as 384- or 1536-well plates. This transfer of liquid between plates having different formats is referred to as "reformatting."

Tools are available for en masse reformatting. En masse reformatting is when the contents of groups of wells or even all the wells of a plate having a first format are transferred, in a single operation, to the wells of a plate having a second format. The devices for doing such en masse reformatting typically use a plurality of syringes (e.g., 8 syringes or 96 syringes are common) that aspirate the contents of the wells of, for example, a 96-well plate, and dispense the aspirated liquid into the wells of higher density plates.

Of late, there has been interest in reformatting on a well-by-well basis. In other words, rather than en masse reformatting, a need has arisen to transfer the contents of a particular well in a source plate to a particular well in a destination plate. The prior art offers little in the way of technology for this application.

One option, at least in theory, for well-to-well reformatting is to reformat manually using a pipette. In practice, this is impractical if not impossible. Aside from an inability to achieve a sufficient throughput rate for commercial scale operation, it is probably beyond the capabilities of a human to accurately or repeatedly pipette liquid into the 1.3 mm wells of a 1536 well plate.

Another solution in the prior art for well-to-well reformatting is to use a single pipette head that is attached to an x-y-z-positioner, such as is described in U.S. Pat. No. 4,979,093 ("the '093 patent") assigned to Cavro Scientific Instruments. The "single channel" (i.e., one pipette) arrangement for dispensing that is described in the '093 patent is depicted herein in FIG. 1.

Arrangement 100 depicted in FIG. 1 includes two variable length arms 102 and 104 that are connected to hinge 106 and to respective pivots 108 and 110. Stepper motors (not shown) that are disposed within pivots 108 and 110 change the length of arms 102 and 104 via friction drive wheels and pinch rollers (not shown). Storage reels (not shown) that are disposed in pivots 108 and 110 accommodate changes in the length of arms 102 and 104. Changing the length of the arms causes movement in the x-y plane.

Receiver 107, which is connected to arms 102 and 104, engages pipette 124. Pipette 124 is operatively connected to z-motion controller 116 via an "actuator/flow tube" (not shown) that is disposed within guide tube 114. The actuator/flow tube slides within actuation guide 114 when actuated by z-motion controller 116. Such sliding movement of the actuator/flow tube causes pipette 124 to move along the z-axis (i.e., vertically).

The actuator/flow tube is also connected to fluid dispenser 118. Fluid dispenser 118 is operative to cause pressure changes within the actuator/flow tube. Negative relative pressure enables pipette 124 to aspirate fluid, such as from wells 128 in source plate 126. Conversely, positive relative pressure enables pipette 124 to dispense aspirated fluid, such as into wells 132 in destination plate 130.

Source plate 126 and destination plate 130 are registered in a known position on a stationary platform (not shown). The x-y-z coordinates of any well 128 in source plate 126 and the x-y-z coordinates any well 132 in destination plate 130 can therefore be determined. To aspirate from well 128A in source plate 126 and then dispense the aspirated liquid into well 132-19 in destination plate 130, computer 120 transmits the corresponding x-y-z coordinates of the source and destination wells to controller 122. Controller 122 converts the coordinates into motor control information that drives the motors (not shown) that control the arms 102 and 104 and the z-motion controller 116.

There are a number of shortcomings or problems with the apparatus described in the '093 patent. In particular, the positioning operation is relatively slow and disadvantageously exhibits characteristically low positioning and dispensing accuracy since all major liquid dispensing functions are operated on a moving, cantilevered liquid carrier (i.e., the pipette).

Moreover, this device introduces inefficiency (i.e., time delays) as a result of the manner in which a series of transfers are effected. That is, liquid transfers are typically sequenced without regard to the relative positions, in successive cycles, of the source and destination wells.

Furthermore, it will be appreciated that the syringe of a reformatter must be washed between dispenses to avoid possible cross contamination. Prior art reformatters and liquid dispensers in general have very inefficient wash cycles. In particular, in such devices, the working pipette is typically transported to and from a wash station, increasing the operating-washing-operating cycle time. Moreover, wash operations require internal and external washing of the working pipette, so that the washing operation creates a substantial waste problem in view of the number of washes involved and the relatively wasteful manner in which wash solution is used.

A need therefore exists for an improved single channel reformatter.

SUMMARY OF THE INVENTION

The present invention provides, in some embodiments, a single channel reformatter that avoids the drawbacks of the prior art. In particular, the present reformatter is fast and has very high positioning and dispensing accuracy. Such speed and accuracy is achieved, in part, by disposing the source and destination plates on a x-y stage. Rapid and precise motion is more readily obtained by moving the plates on a x-y stage than by moving a pipette at the end of a cantilevered arrangement as in the prior art.

Moreover, in some embodiments of the present invention, the liquid transfer vehicle (i.e., pipette, syringe, etc.) is limited to z-axis motion and, in fact, is mechanically de-coupled from the x-y stage. A repeatable, accurate dispensing operation is more readily obtained with a syringe, etc., that is stationary in the x-y plane than with one that is moving in three dimensions at the end of a cantilevered arrangement as in the prior art.

In a further embodiment, the present invention provides an efficient wash system that advantageously operates between successive plate-to-plate transfer operations (hereinafter "normal liquid transfer operations" or "working cycle"). Since, in accordance with the present teachings, the liquid transfer vehicle does not travel in the x-y plane during the working cycle, it can be, and advantageously is, integrated directly into such a wash system. In such an integrated system, no time is lost, as with prior art dispensers, in moving the liquid transfer vehicle to a wash station and back again for the subsequent working cycle.

In some embodiments, the wash system comprises two syringes—a wash syringe and a waste syringe—in addition to the liquid transfer vehicle. In such embodiments, the liquid transfer vehicle is advantageously configured as a syringe (hereinafter the "working syringe"). The three syringes are in fluidic communication with one another and with supply and waste reservoirs. Further, the three syringes and their plungers cooperate mechanically with a single drive mechanism such that a "stroke" of the drive aspirates (dispenses) the working syringe and the waste syringe while, at the same time, the wash syringe is dispensed (aspirated). Moreover, in some embodiments, the drive element that actuates the plungers during the wash cycle is used during normal liquid transfer operations.

The present invention also provides a method for controlling the reformatting operation. The method advantageously comprises: (1) specifying well-to-well links, (2) determining a preferred execution order for executing the specified links thereby enhancing reformatting efficiency, and (3) executing the specified links in the preferred order. In some embodiments, the preferred execution order sequences links based on the relative locations of "destination wells" (i.e., wells that receive liquid from the source plate) in successive cycles.

DETAILED DESCRIPTION

The illustrative embodiments of the present invention that are described herein and depicted in the accompanying drawings are directed to a single channel reformatter. This Detailed Description begins with a description of the functional elements of such a single channel reformatter. This approach is useful for pedagogical purposes in that it provides increased clarity of presentation and generality of description.

The description of functional elements is followed by a description of several specific structural embodiments. It should be understood that the specific structural embodiments are provided by way of illustration, not limitation. Moreover, the principles, apparatuses and methods described in this Specification have applicability beyond the illustrated reformatting application. For example, a wash system and x-y-z positioning system disclosed herein may suitably be used to improve the operation of a variety of liquid-handling apparatuses. And, with modifications that are within the capabilities of those skilled in the art, the principles, apparatus and methods described herein are readily extended to applications other than liquid handling. Such variations and modifications are within the contemplated scope of the present invention.

Figure 1:
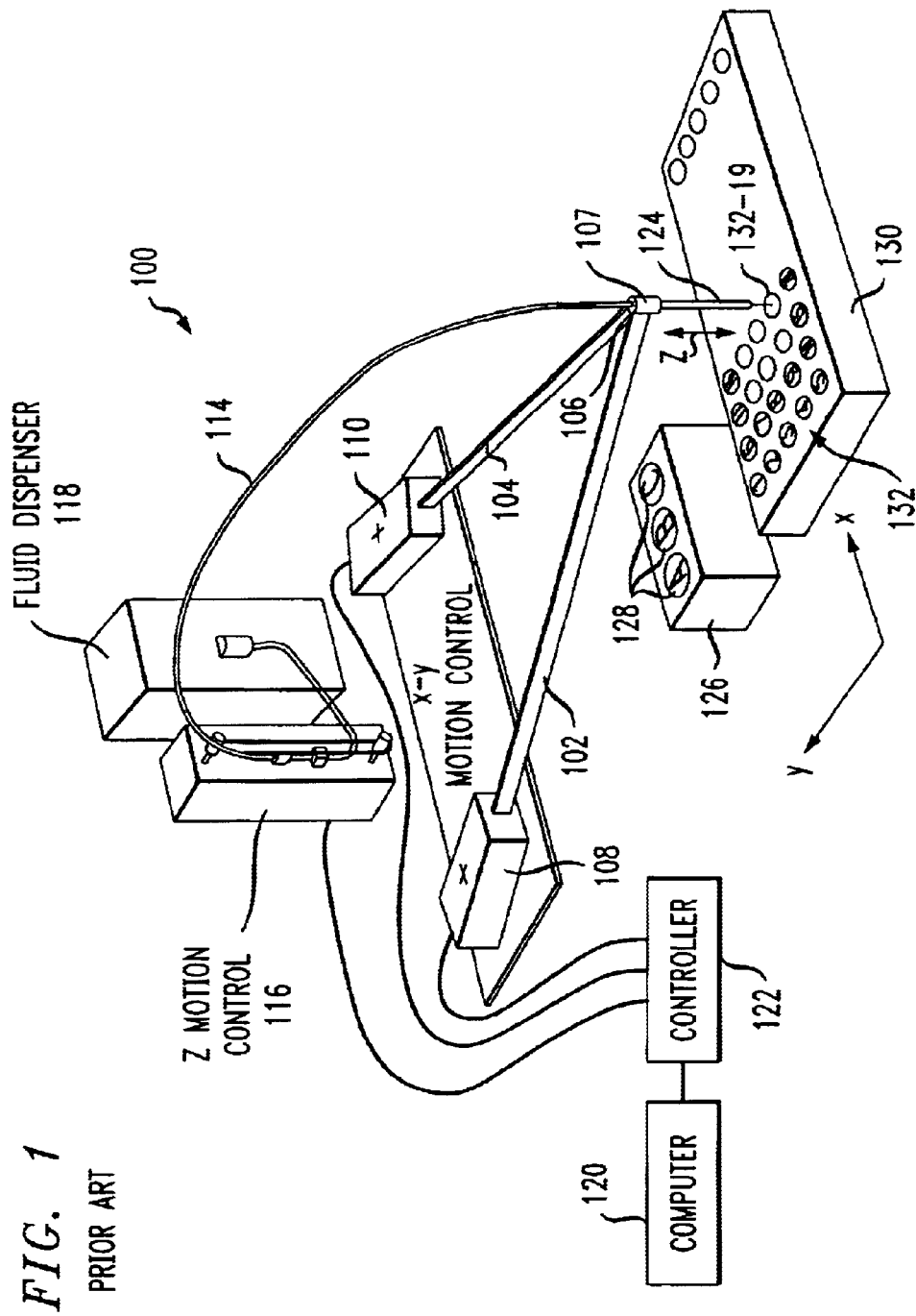
FIG. 1 depicts an arrangement for single channel reformatting in the prior art.
Figure 2:
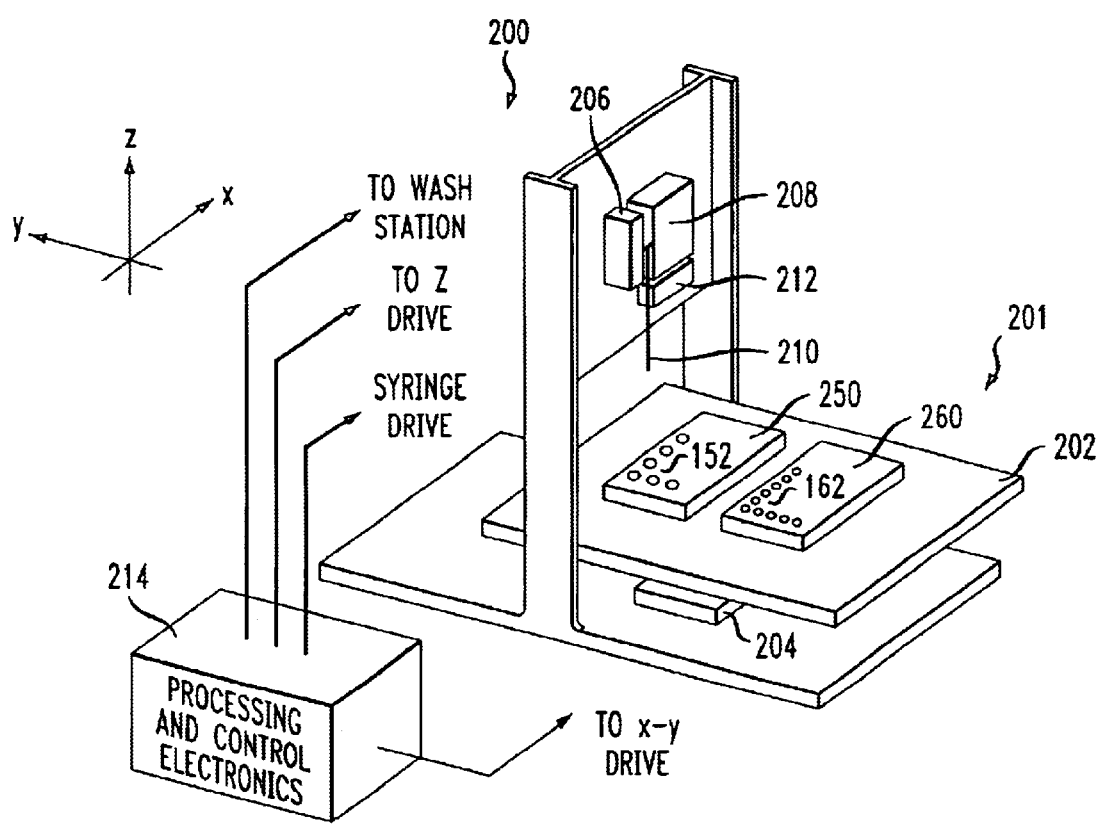
FIG. 2 depicts a conceptual or figurative view of an illustrative embodiment of a single channel reformatter in accordance with the present invention.

FIG. 2 depicts an illustrative single channel reformatter ("SCR") 200 in accordance with the present teachings. Illustrative SCR 200 includes x-y positioner 201, z-positioner 206, optional integrated wash station 208, liquid transfer vehicle 210, fluid control device 212, and processing and control electronics 214, interrelated as shown.

Z-positioner 206 is operable to move liquid transfer vehicle 210 upwardly and downwardly (i.e., along the z-axis) as directed by processing and control electronics 214. The term "liquid transfer vehicle," as used herein, means syringe, pipette, capillary tube, nozzle or like element suitable for delivering (possibly in conjunction with an element for causing aspirating or dispensing flow) a desired amount of liquid at a desired location. In the illustrated embodiments, the liquid transfer vehicle is a syringe, and will henceforth be referred to as "working syringe 210." Working syringe 210 is moved downwardly, for example, in preparation for dispensing liquid into a container positioned beneath it, and moved upwardly to allow that container to be moved away to allow another container to take its place.

The x-y positioner 201 comprises x-y drive 204 that is operable, when actuated, to precisely and accurately move x-y stage 202 in the x-y plane. In the illustrated embodiment, x-y stage 202 comprises a surface that is suitable for receiving source container 250 from which liquid is aspirated. Stage 202 is also suitable for receiving destination container 260 into which the aspirated liquid is dispensed. In the embodiments described herein, source container 250 is a micro-titer plate having a plurality of wells 152 and destination container 260 is a micro-titer plate having a plurality of wells 162. It should be understood, however, that other types of containers may suitably be used in conjunction with the present invention.

With source plate 250 and destination plate 260 disposed on x-y stage 202, x-y positioner 201 is operable to: (1) position any of the wells 152 of plate 250 under working syringe 210 so that liquid contained in such wells can be aspirated into working syringe 210, and (2) position any of the wells 162 of plate 260 under working syringe 210 so that liquid that has been aspirated into syringe 210 can be dispensed into such wells.

To perform well-to-well liquid transfer operations, the spatial location of each well must be known. To that end, x-y stage 202 has physical adaptations (not shown in FIG. 2) for receiving plates 250 and 260 at predetermined locations. Given a particular plate format (e.g., 96-well, 384-well, etc.) and the location of the plate at either the source plate position or at the destination plate position on x-y stage 202, the spatial location of each well, in terms of x, y and z coordinates, is readily determined.

When appropriately positioned in a specified well 152 in source plate 250 by the action of positioners 201 and 206, a suction (i.e., negative relative pressure) is developed in working syringe 210 to aspirate a desired amount of liquid from that well. After aspirating the liquid, working syringe 210 is moved vertically (i.e., along the z-axis) out of the well. The x-y stage 202 is then advanced to move a specified well 162 in destination plate 260 in to position beneath working syringe 210. Working syringe 210 then moves downwardly under the action of z-positioner 206. Once in position in well 162, the fluid within working syringe 210 is dispensed.

The aspirating and dispensing ("fluid control") functions of syringe 210 are accomplished via fluid control device 212. The term "fluid control device," as used herein, means pump, vacuum pump, ejector, or other arrangement capable for generating aspirating or dispensing flow through the liquid transfer vehicle (e.g., working syringe 210). Since, in the illustrated embodiments, a syringe (as opposed to a pipette, etc.) is used as the liquid transfer vehicle, the fluid control functions are advantageously implemented by simply drawing the plunger away from the bottom of body of the syringe, or pushing it towards the bottom of the body of the syringe. Thus, the meaning of the term "fluid control device" also encompasses a mechanism suitable for moving the plunger in the aforementioned fashion. In recognition of the fact that the illustrated embodiments depict a syringe as the liquid transfer vehicle, the fluid flow controller will henceforth be referred to as "syringe drive 212." The term "syringe drive," as used herein, thus refers to a mechanism suitable for moving the plunger in the aforementioned fashion. Those skilled in the art will recognize that many mechanisms are suitable for such service. By way of illustration, not limitation, the embodiments depicted herein utilize a linear drive mechanism for this purpose. As used herein, the term "linear drive mechanism" refers to any mechanism capable of moving an object in linear motion.

Z-positioner 206, x-y positioner 201 and syringe drive 212 are actuated by processing and control electronics 214. The processing and control electronics, which is capable of performing the functions described below, is suitably implemented using either shared or dedicated hardware, including, without limitation, hardware capable of executing software.

Provided with "link data" specified by a user (e.g., transfer liquid from the well located in the source plate at row 2, column 7 to destination well (15,20), etc.), the spatial coordinates of the wells involved in the transfer, and several other control parameters described later, processing and control electronics 214 is operable to:

(1) actuate x-y positioner 201 to move a well 152 into position under syringe 210;

(2) actuate z-positioner 206 to lower working syringe 210 into well 152;

(3) actuate syringe drive 212 to aspirate liquid from well 152 into working syringe 210;

(4) actuate z-positioner 206 to raise working syringe 210 out of well 152;

(5) actuate x-y positioner 201 to move a well 162 into position under syringe 210;

(6) actuate z-positioner 206 to lower working syringe 210 into well 162;

(7) actuate syringe drive 212 to dispense liquid from syringe 210 into well 162; and (8) actuate z-positioner 206 to raise working syringe 210 out of well 162.

To the extent that different fluids are being handled in subsequent liquid handling cycles, cross contamination will occur unless working syringe 210 is washed. To that end, working syringe 210 is advantageously washed via wash system 208 after an aspirating/dispensing cycle. Wash station 208 advantageously washes the inside and the outside of working syringe 210 to substantially reduce the risk of cross contamination. Processing and control electronics 214 controls the wash operation.

As already discussed, working syringe 210 is advantageously not moved in the x-y plane. As a consequence, in some embodiments of the present invention, working syringe 210 is incorporated directly into wash system 208. A first benefit of such incorporation is that time is saved by not having to transfer working syringe 210 to a wash station and back again. A second benefit of such incorporation is that, when wash station 208 is appropriately configured, syringe drive 212 advantageously provides both the fluid control function during normal liquid transfer operations and also drives the wash station operations. An illustrative embodiment of wash system 208 and its workings is described later in this Specification.

This Specification continues with a description of FIGS. 3–14, which provide illustrative structural details for the functional description provided above. Structures depicted in these Figures will be cross-referenced, as appropriate, to the more functional representations provided in FIG. 2.

Figure 3:
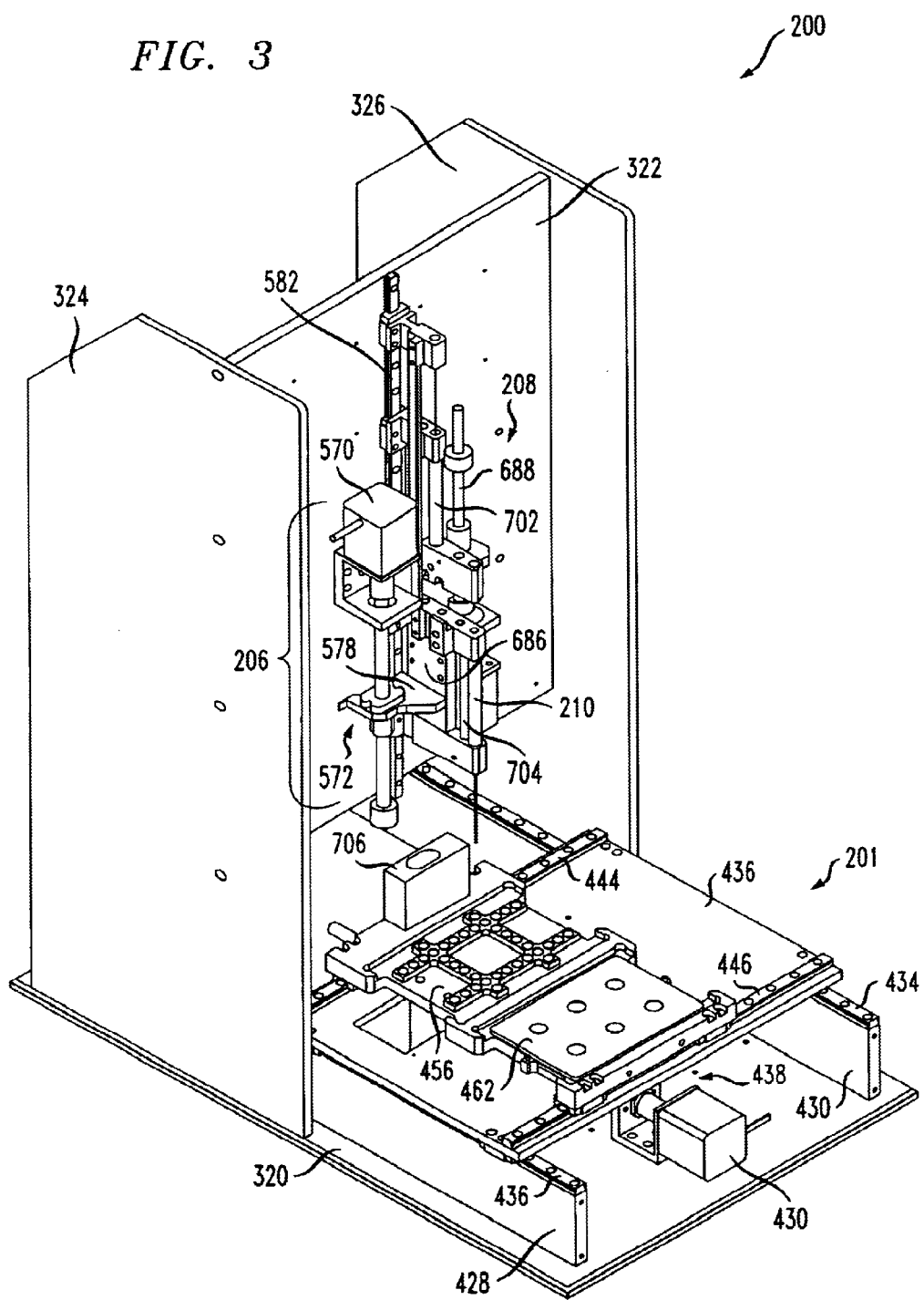
FIG. 3 depicts a specific embodiment of the reformatter depicted in FIG. 2.

FIG. 3 depicts an embodiment of SCR 200. The various positioning, dispensing and wash structures that comprise SCR 200 are advantageously anchored by a frame comprising base plate 320, back plate 322, left side 324 and right side 326, interrelated as shown in FIG. 3. Base plate 320 provides support for the x-y positioner 201 and back plate 322 provides support for z-positioner 206 and wash system 208. Left side 324 and right side 326 support back plate 322.

Figure 4:
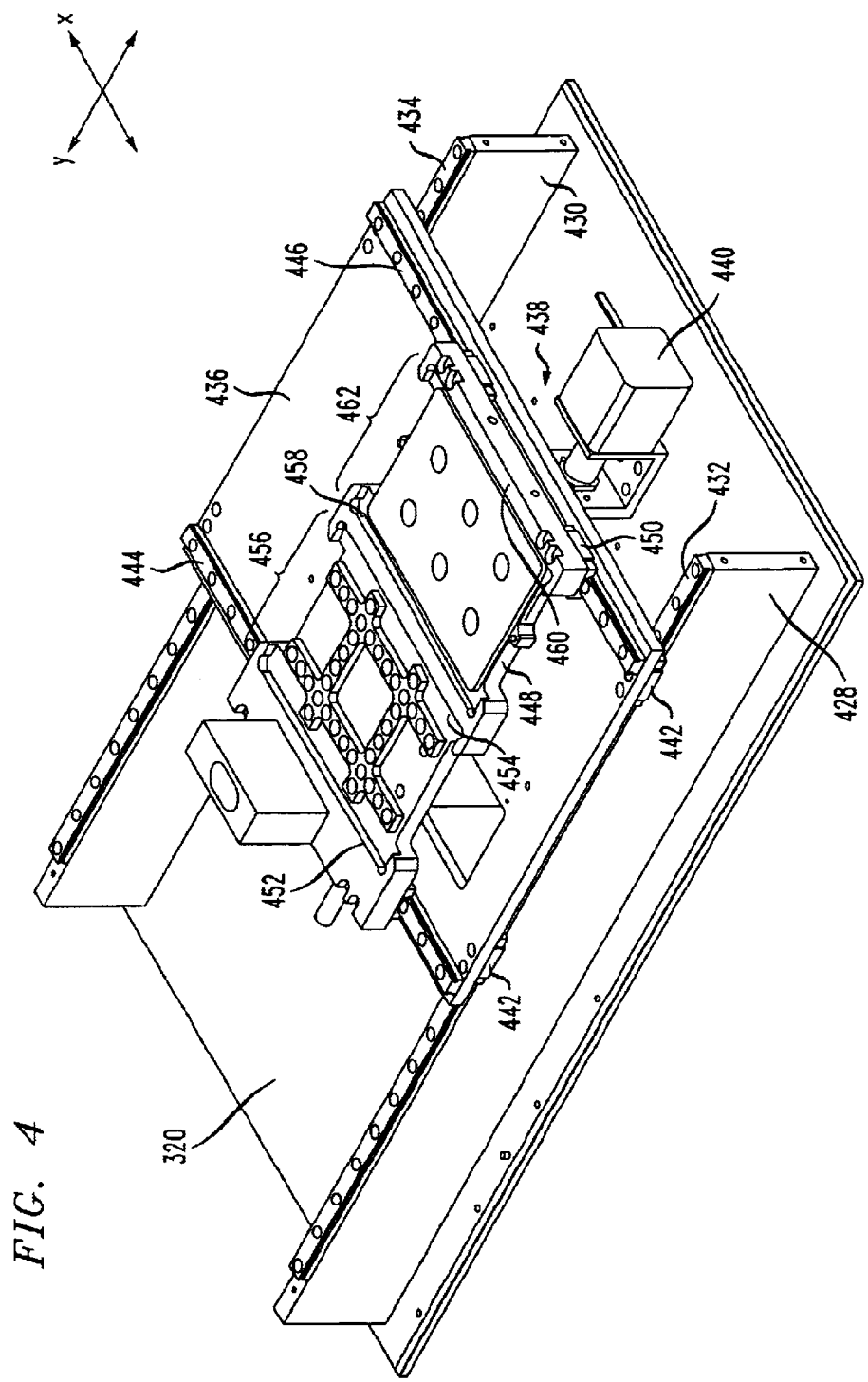
FIG. 4 depicts the x-y positioner of the single channel reformatter of FIG. 3.

The x-y positioner 201, which, for the sake of clarity, is depicted sans z-positioner 206 and wash station 208 in FIG. 4, comprises an x-positioner "piggybacked" on a y-positioner. The y-positioner includes y-plate or y-stage 436 and two linear bearings 432 and 434 that are disposed on respective bearing spacers 428 and 430. The bearing spacers 428 and 430, which are attached to base plate 320 near the edges of the long sides thereof, raise linear bearings 432 and 434 (and y-plate 436) above base plate 320 to allow room for underlying y-drive 438 and the x-drive (not shown).

Slides 442 are mounted on the underside of y-plate 436 so that they engage linear bearings 432 and 434. Slides 442 promote low-friction movement of y-plate 436 over linear bearings 432 and 434. Y-drive 438 controls the movement of y-plate 436 along the linear bearings. In the illustrated embodiment, y-drive 438 is configured as a linear drive mechanism. The particular linear drive mechanism depicted comprises y-stepper motor 440 that drives a ball screw assembly (not shown in FIG. 4) in well-known fashion. Y-stepper motor 440 is attached to base plate 320 and the ball screw assembly is engaged to the underside of y-plate 436. Y-plate 436 is driven along linear bearings 432 and 434 along the y-axis as y-stepper motor 440 turns, as dictated by processing and control electronics 214 (FIG. 2).

Linear bearings 432, etc., slides 442, etc., and the ball screw assembly are available from NSK Corporation of Schaumberg, Ill. Machined parts, such as bearing spacers 428, etc., can be fabricated to specification by Manheim Corporation of Collegeville, Pa. Stepper motor 440 is available from Applied Motion Products of Watsonville, Calif.

The x-positioner, which is piggybacked on the y-positioner, includes x-plate or x-stage 448 and two linear bearings 444 and 446 that are disposed near the edges of the long sides of y-plate 436. Slides 450 are mounted on the underside of x-plate 448 so that they engage linear bearings 444 and 446 to facilitate low-friction movement of x-plate 448. The x-drive (not depicted) controls the movement of x-plate 448 along linear bearings 444 and 446. In some embodiments, the x-drive is configured as a linear drive mechanism (not shown), such as the combination of a stepper motor driving a ball screw assembly.

As previously described, x-plate 448 has physical adaptations for receiving source containers 250 and destination containers 260 at predetermined locations. In the illustrated embodiment, the containers 250, 260 are micro-titer plates, and the physical adaptations are guides 452 and 454 that define source plate receiver 456 and guides 458 and 460 that define destination plate receiver 462, both appropriately sized and shaped for receiving micro-titer plates. In other embodiments (not shown), the guides are movable such that the size of the receiver can be changed to accommodate containers other than plates. In still other embodiments, the guides are replaced with various clamping devices as may be appropriate for receiving certain types of liquid containers.

Figure 5:
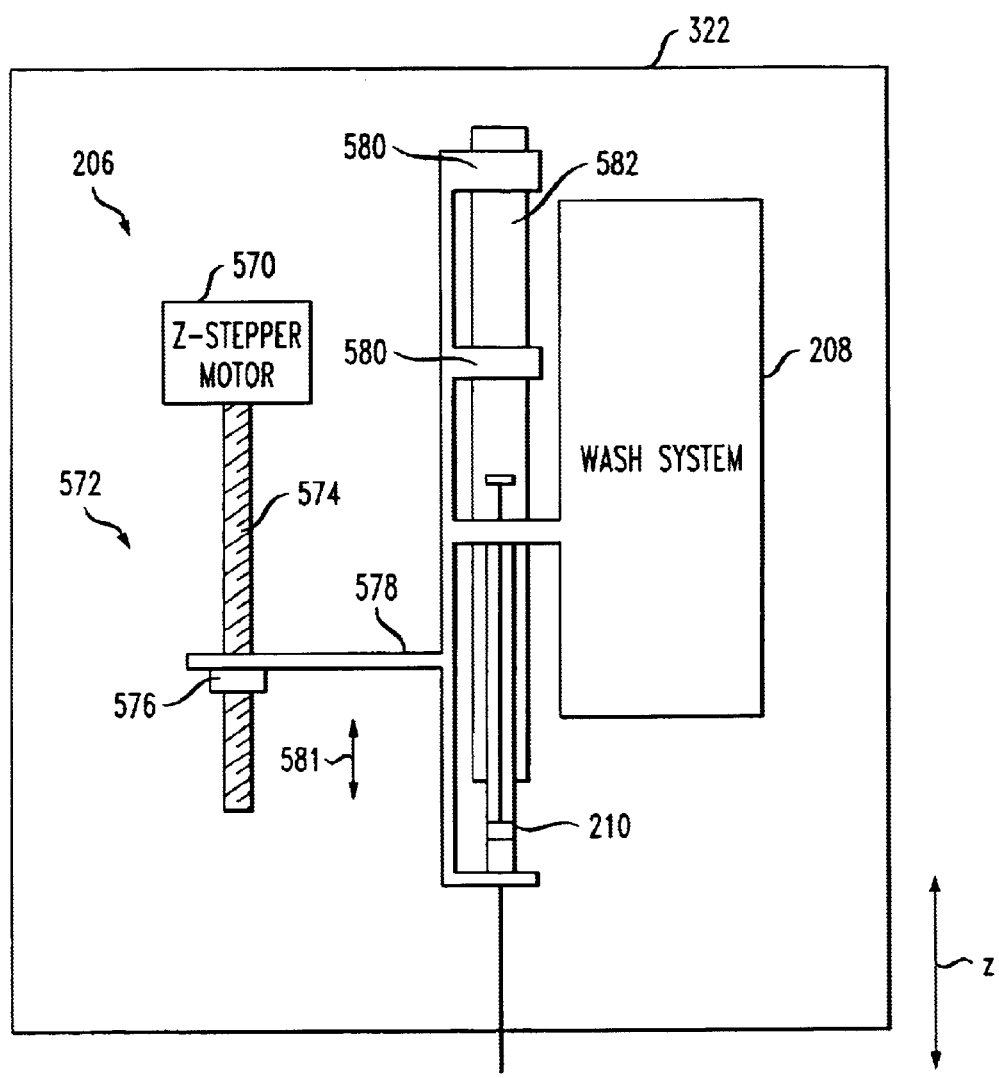
FIG. 5 depicts a conceptual or figurative view of an illustrative embodiment of a z-positioner for use in conjunction with the single channel reformatters of FIGS. 2 and 3.
Figure 6:
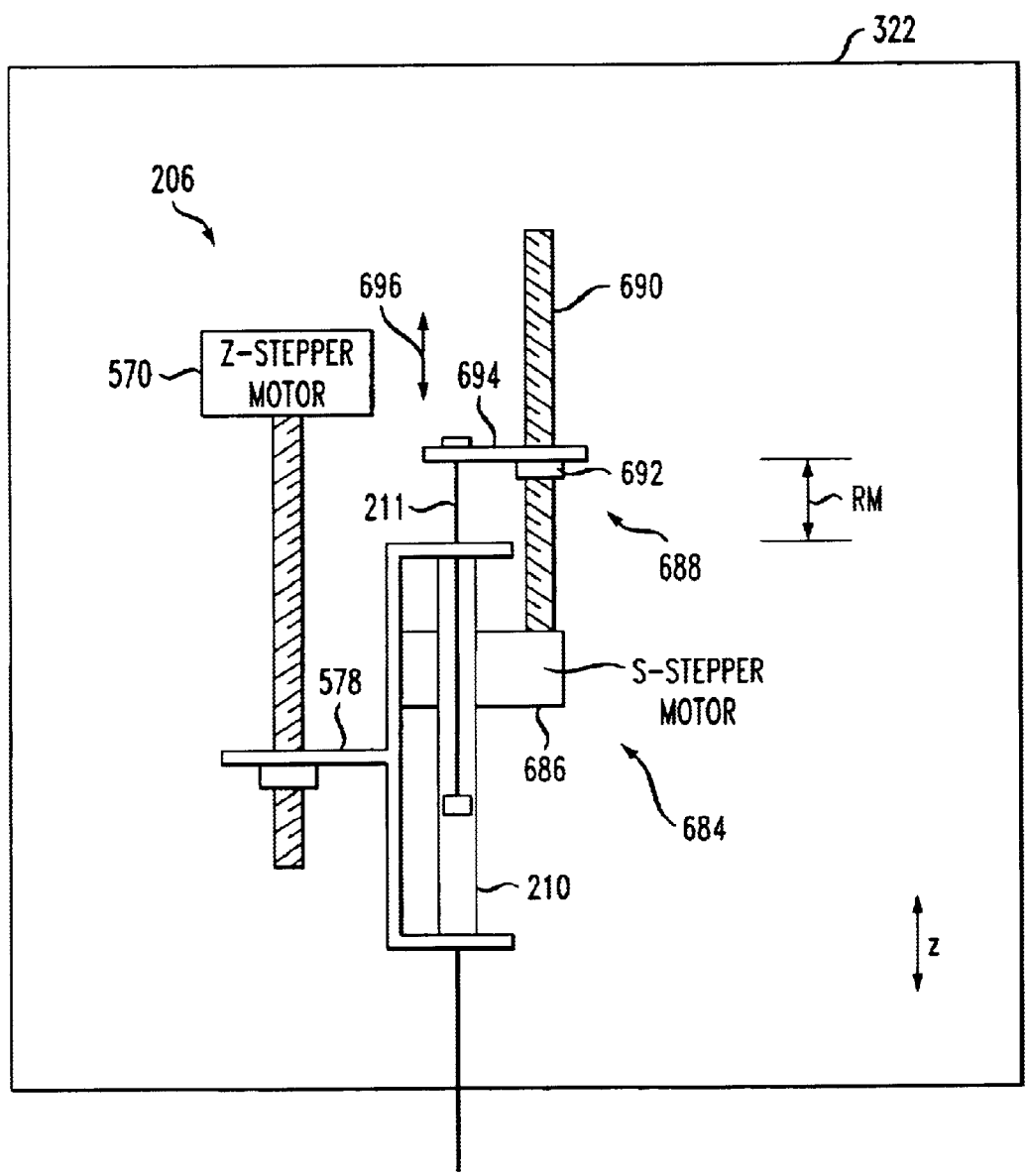
FIG. 6 depicts the z-positioner of FIG. 5 as well as a syringe drive for causing aspirating and dispensing action in the working syringe.

Illustrative z-positioner 206 is depicted, sans x-y positioner 201, in FIGS. 5 and 6. Z-positioner 206 is depicted, in the illustrative embodiment, as a linear drive mechanism. The particular linear drive mechanism shown comprises z-stepper motor 570 driving ball screw assembly 572.

As depicted in FIG. 5, working syringe 210 is secured to frame 578, which, in turn, is operatively engaged to ball screw assembly 572. Specifically, in the illustrated embodiment, screw or shaft 574 receives frame 578 in sliding engagement above ball nut 576. Frame 578 is also slidingly engaged (via slides 580 that depend from frame 578) to linear bearing 582, which is itself attached to back plate 322. As a consequence, frame 578 slides over linear bearing 582 along direction vector 581 (i.e., along the z-axis) as urged by ball nut 576 on screw 574 under the action of z-stepper motor 570.

As previously mentioned, in some embodiments of the present invention, working syringe 210 is integrated into wash system 208. In those embodiments, it is advantageous to mechanically link wash system 208 to frame 578 so that appropriate elements of wash system 208 move in concert with working syringe 210. In other words, as a result of such a connection, there is no relative motion between wash system 208 and working syringe 210. Such a mechanical link is depicted figuratively in FIG. 5.

FIG. 6 depicts z-positioner 206 and syringe drive 684 disposed on back plate 322. Syringe drive 684 provides fluid control functions (i.e., aspirating and dispensing) for working syringe 210. Syringe drive 684 can be, for example, a linear drive mechanism like the x-, y- and z-drives previously described. In the illustrated embodiment, syringe drive 684 comprises s-stepper motor 686 and ball screw assembly 688.

Syringe drive 684 operatively engages plunger 211 of working syringe 210. In particular, in the illustrated embodiment, coupling member 694 engages plunger 211 of working syringe 210 while screw 690 receives coupling member 694 in sliding engagement above ball nut 692. As a result of such engagement, coupling member 694 and plunger 211 are moved along direction vector 696 (ie., along the z-axis) responsive to movements of ball nut 692 on screw 690 under the action of s-stepper motor 686. Coupling member 694, and any other structural members (e.g., plates, etc.), may suitably be formed from anodized aluminum.

As previously indicated, in some embodiments, syringe drive 684 is advantageously used to drive wash systems operations, as well as normal liquid transfer operations. In such embodiments, syringe drive 684 is advantageously piggybacked on z-positioner 206 such that syringe drive 684 moves with syringe 210 on z-axis movements. This arrangement is illustrated in FIG. 6 (see attachment of s-stepper motor 686 to frame 578).

It should be understood that, in the illustrated embodiment, syringe drive 684 does NOT change the position of working syringe 210. Rather, syringe drive 684 changes the position of plunger 211. Syringe drive 684 therefore causes a relative motion RM between the body of the syringe 210 and plunger 211. Upward movement of plunger 211 thus generates a suction flow that causes any liquid in contact with the tip of working syringe 210 to be aspirated therein. Downward movement of plunger 211 generates a positive pressure that forces any liquid that is within working syringe 210 to be dispensed therefrom. And, as previously noted, in embodiments in which syringe drive 684 is piggybacked on z-positioner 206 and therefore moves along with working syringe 210, the z-positioner is not operative to cause a relative motion between plunger 211 and working syringe 210. In other words, z-positioner 206 does not generate any aspirating or dispensing action in working syringe 210.

In embodiments in which working syringe 210 is integrated into wash system 208, any movement of plunger 211 relative to the body of working syringe 210 during liquid transfer operations will affect flow conditions in wash system components. Those effects will be described later in this Specification.

Figure 7:
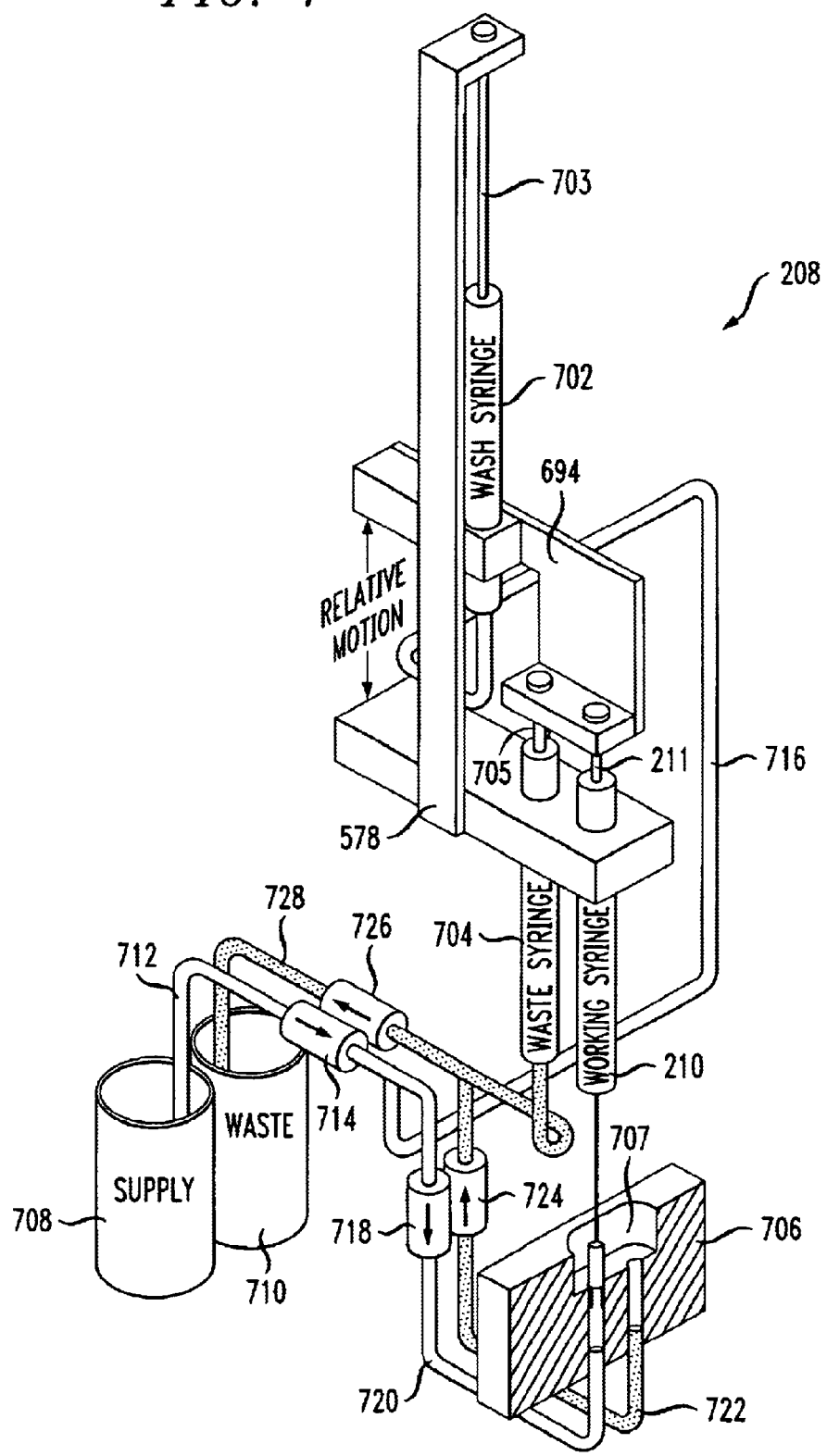
FIG. 7 depicts an illustrative embodiment of a wash system in accordance with the present teachings.

FIG. 7 depicts an illustrative embodiment of wash system 208 in accordance with the present teachings. For clarity of illustration, syringe drive 684 is not shown in FIG. 7. For reference, syringe drive 684 engages coupling member 694 (as illustrated in FIG. 6). For further perspective, see FIG. 3, wherein wash system 208 is depicted in conjunction with other elements of illustrative SCR 200.

Illustrative wash system 208 includes two syringes in addition to working syringe 210.

The additional syringes include wash syringe 702 having plunger 703 and waste syringe 704 having plunger 705. Wash syringe 702 supplies cleaning fluid to working syringe 210, while waste syringe 704 provides a suction flow that removes contaminated cleaning fluid from well 707 in wash/waste station 706 after it is has been used to wash working syringe 210.

Illustrative wash system 208 also includes supply reservoir 708 and waste reservoir 710. Supply reservoir 708 supplies cleaning fluid to wash syringe 702, and waste reservoir 710 receives the contaminated cleaning fluid that waste syringe 704 has aspirated from well 707. The supply reservoir and the waste reservoir may suitably be realized as standard flasks.

Various conduits place the various syringes in fluid communication with supply reservoir 708, waste reservoir 710 and wash/waste station 706. Wash/waste station 706 is made out of a material that is selected for chemical compatibility with the cleaning fluid and various reagents. Polyethylene has been found to be an acceptable material for most applications.

In accordance with the present teachings, plunger 211 of working syringe 210 and plunger 705 of waste syringe 704 cooperate mechanically with coupling member 694 such that those two syringes aspirate together and dispense together. On the other hand, wash syringe 702 and its plunger 703 are configured such that wash syringe 702 aspirates while the waste and working syringe dispense, and wash syringe 702 dispenses while the waste and working syringe aspirate. In accordance with some embodiments of the present invention, plungers 211, 705 and 703 are all moved by the same actuating device (i.e., syringe drive 684) at the same time.

The operation of wash station 208 is now described with reference to the flow of cleaning fluid through the wash system as a function of syringe drive movements, as depicted in FIGS. 7 and 8A–8C.

Figure 8C:
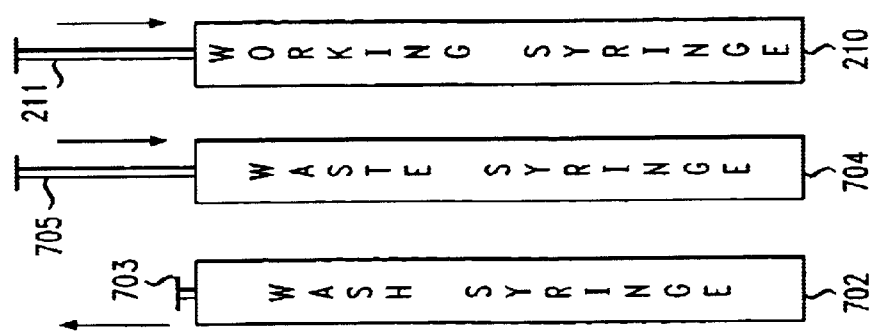
FIGS. 8A–8C depict the position of the plunger and the direction of its movement within each of the three syringes comprising the illustrative wash system of FIG. 7.
Figure 8B:
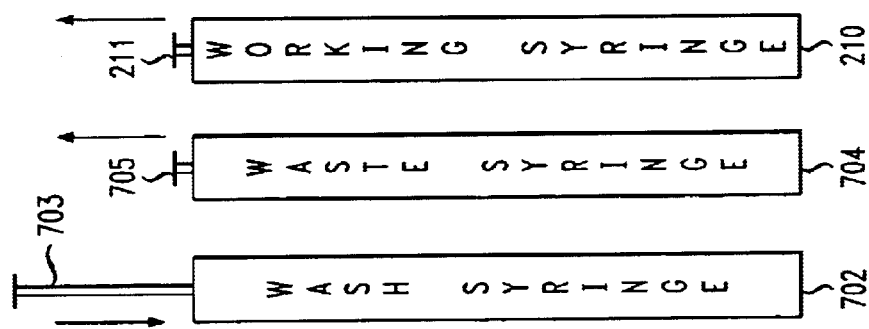
Figure 8A:
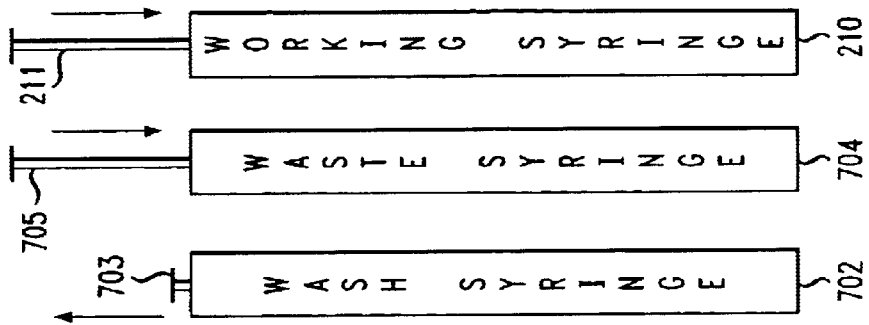

FIG. 8A depicts the "state" of the three syringes, and their associated plungers, at the beginning of the previous operation (i.e., before the wash cycle) wherein working syringe 210 is about to dispense reagent into destination plate 260. As depicted in FIG. 8A, as plunger 211 is moved downwardly (via the action of syringe drive 684) so that working syringe 210 can dispense reagent into a well in a destination plate, plunger 703 is moved upwardly (via the same movement of syringe drive 684).

As plunger 703 moves upwardly creating a suction flow, check valve 714 opens and check valve 718 closes due to the one-way nature of such check valves. With check valve 714 open, cleaning fluid is aspirated from supply reservoir 708 through reservoir supply conduit 712 and through wash syringe conduit 716 into wash syringe 702. The check valves, which should have a low cracking pressure (1.5 psi has been found to be acceptable), are available from Upchurch Scientific of Oakharbor, Wash. All conduit used in wash system 208 should be selected for chemical compatibility with the chemicals being used. Teflon is suitable for many applications.

As plunger 211 of working syringe 210 is forced downwardly, plunger 705 of waste syringe 704 is also forced downwardly. As this occurs, any used cleaner that had been drawn into waste syringe 704 (see description accompanying FIG. 8B) is dispensed, closing check valve 724 and opening check valve 726. With check valve 726 open, used cleaning fluid is forced through waste reservoir conduit 728 into waste reservoir 710.

Note the efficiency provided by (1) the integration of working syringe 210 into wash station 208; and (2) driving both working syringe 210 and wash system 208 with syringe drive 684. In particular, wash system 208 is advantageously readying for the next wash cycle during normal liquid transfer operations and is actuated by the same drive that is dispensing working syringe 210 during normal liquid transfer operations.

FIGS. 7 and 8B depict the state of the three syringes and their plungers after reagent has been dispensed from working syringe 210 into destination plate 260. In FIG. 7, wash/waste station 706 has been positioned under working syringe 210 via x-y positioner 201, and z-positioner 206 has dropped working syringe 210 into working syringe supply conduit 720. Working syringe 210 is therefore ready to aspirate cleaning fluid.

As plunger 703 is moved into wash syringe 702 (via the action of syringe drive 684), cleaning fluid is dispensed therefrom. Due to the flow of cleaning fluid out of wash syringe 702 and through wash syringe conduit 716, check valve 714 closes and check valve 718 opens. With check valve 718 open, cleaning fluid flows into working syringe supply conduit 720. As plunger 703 moves into wash syringe 702, plunger 211 moves upwardly out of working syringe 210. This upward movement creates a suction flow that aspirates cleaning fluid into working syringe 210. Also, as a consequence of its position partially within working syringe supply conduit 720, the exterior of the needle or tip of working syringe 210 is washed with cleaning fluid.

Waste syringe 704 aspirates with working syringe 210. The upward movement of plunger 705 creates a suction flow that opens check valve 724 and closes check valve 726. Contaminated cleaning fluid in well 707 is drawn into waste supply return conduit 722, through check valve 724 and into waste syringe 704.

FIG. 8C depicts the state of the three syringes and their plungers after cleaning fluid is dispensed from wash syringe 702 and aspirated by working syringe 210. During the next operation, contaminated cleaning fluid is dispensed from working syringe 210. In preparation for this operation, z-positioner 206 raises working syringe 210 out of working syringe supply conduit 720.

As plunger 211 is moved downwardly into working syringe 210 (via the action of syringe drive 684), contaminated cleaning fluid is dispensed from the working syringe into well 707. Moreover, waste syringe 704 dispenses its load of contaminated cleaning fluid (see description accompanying FIG. 8B) through check valve 726 and waste reservoir conduit 728 into waste reservoir 710. At the same time, wash syringe 702 aspirates fresh cleaning fluid in the manner previously described (see description accompanying FIG. 8A).

After contaminated cleaning fluid is dispensed from working syringe 210, the next reformatting cycle is ready to begin. And, as the next reformatting cycle begins with working syringe 210 aspirating liquid from a source well, wash syringe 702 dispenses fresh cleaning fluid to working syringe supply conduit 720 thereby forcing any contaminated cleaning fluid in conduit 720 into well 707. Meanwhile, waste syringe 704 aspirates the contaminated cleaning fluid from well 707. As previously noted, integrating working syringe 210 into wash system 208, and using a single drive to "power" both working syringe 210 and wash system 208 provides an extraordinary level of efficiency to the washing operation, in accordance with the present teachings.

The foregoing specific embodiment is generalized by the following description of wash system 208. In accordance with the present teachings, wash system 208 includes:

a first conduit (conduits 712 and 720) that is in fluid communication with a supply of cleaning fluid (supply reservoir 708) and wash/waste station 706;

a second conduit (conduits 722 and 728) that is in fluid communication with wash/waste station 706 and waste reservoir 710; and a fluid flow controller (syringe drive 684 in conjunction with the plungers/syringes and conduit 716) for:
generating a flow of cleaning fluid from supply reservoir 708 to said wash/waste station 706, and
generating a flow of contaminated cleaning fluid from said wash/waste station 706 to said waste reservoir 710.

To ensure proper flow of cleaning fluid through wash system 208, which is a closed system, waste syringe 704 should have a greater capacity than wash syringe 702 and the wash syringe has a greater capacity than working syringe 210. By way of example, capacities of 590, 250 and 100 microliters for waste syringe 704, wash syringe 702 and working syringe 210, respectively, have been found to be suitable for use in wash system 208. The syringes should be high quality, glass syringes such as Hydra syringes, available from Robbins Scientific Corporation of Sunnyvale, Calif.

Figure 9:
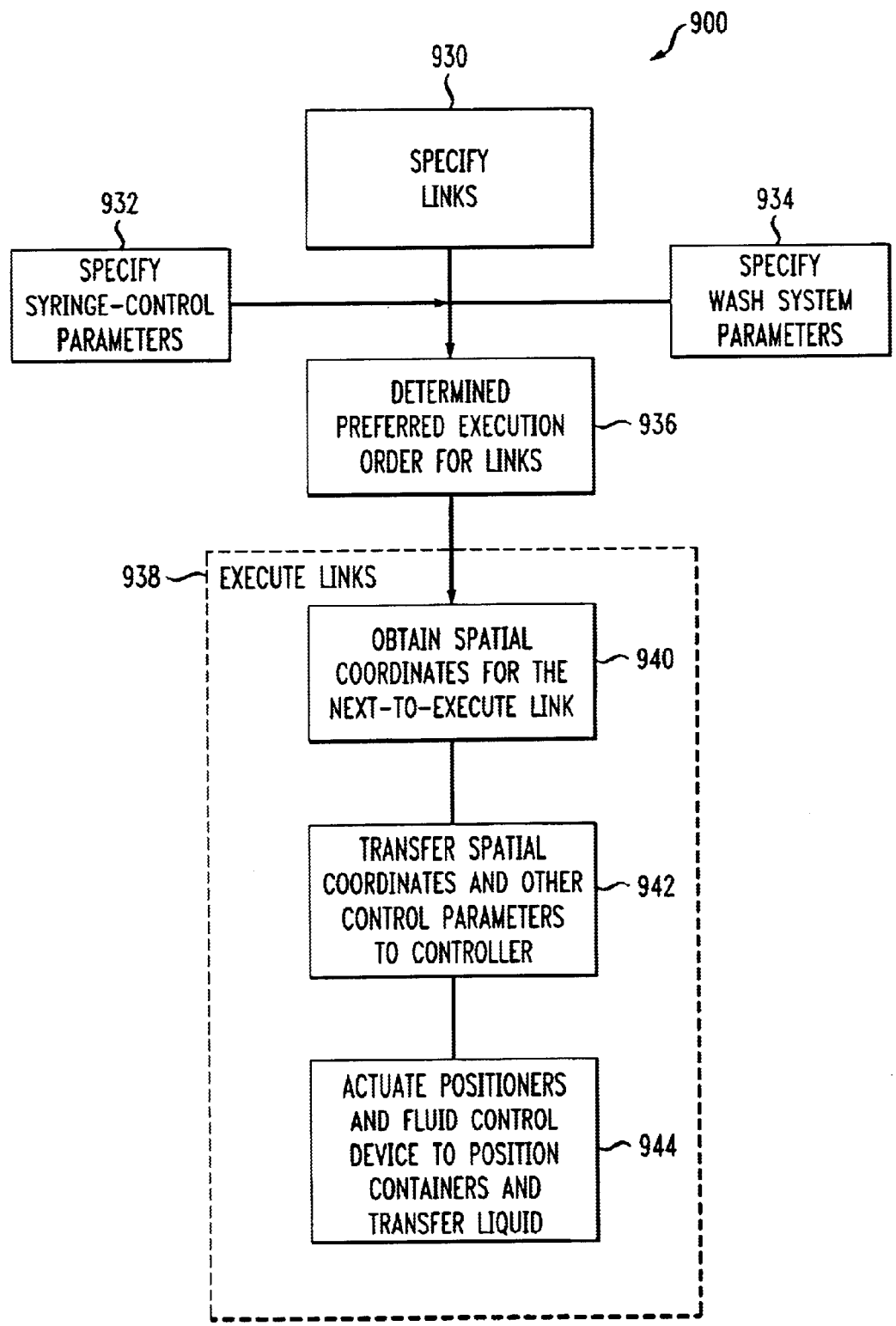
FIG. 9 depicts a method for operating the present single channel reformatter.

FIG. 9 depicts method 900 for controlling SCR 200. Method 900 is advantageously implemented via processing and control electronics 214, an illustrative embodiment of which is depicted in FIG. 10.

Figure 10:
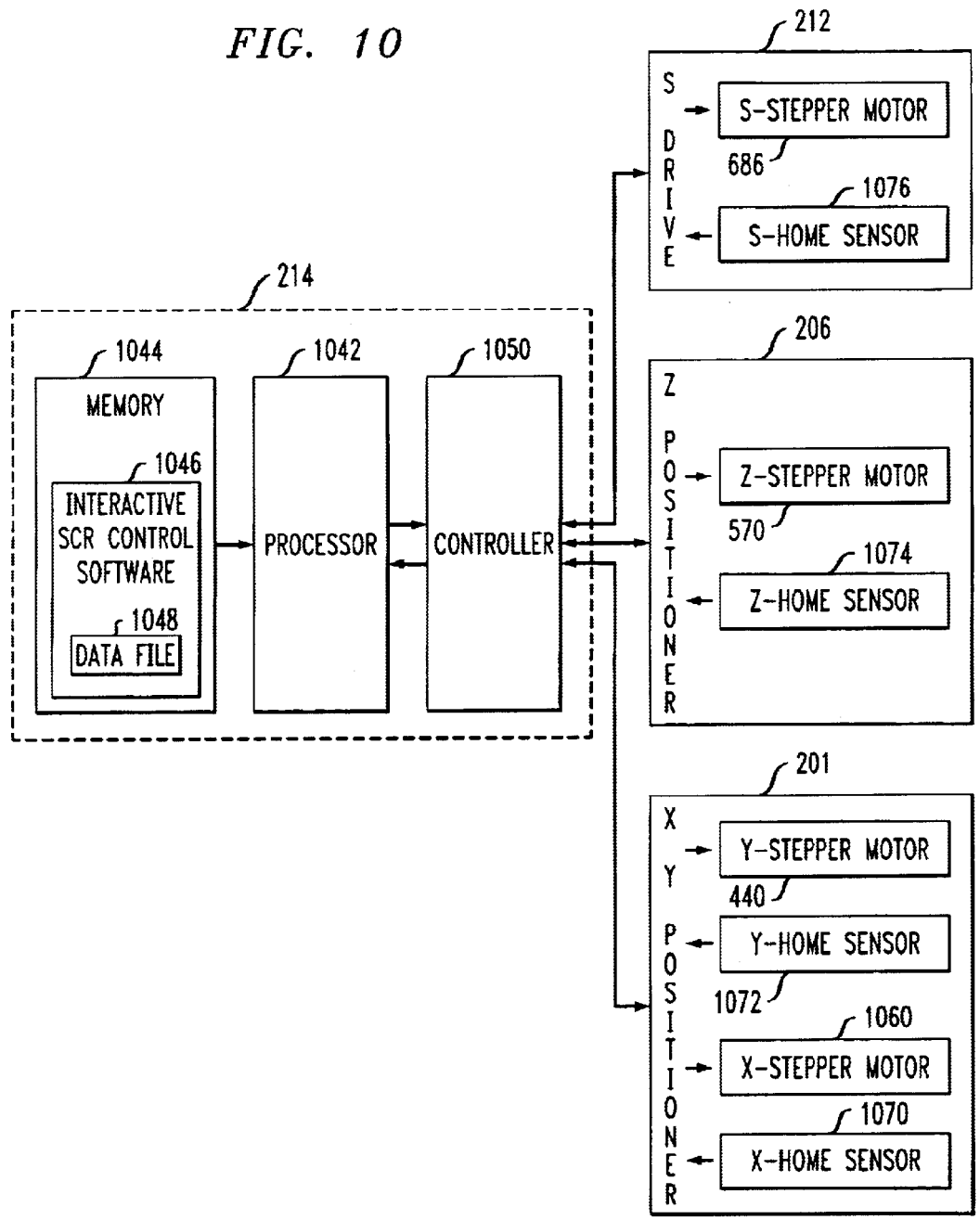
FIG. 10 depicts processing and control electronics for controlling the various positioners and drives used in conjunction with the present single channel reformatter.

In the illustrative embodiment depicted in FIG. 10, processing and control electronics 214 includes processor 1042 running interactive SCR control software 1046. The SCR control software, including updateable data file 1048, is stored in memory/computer storage device 1044.

Figure 11:
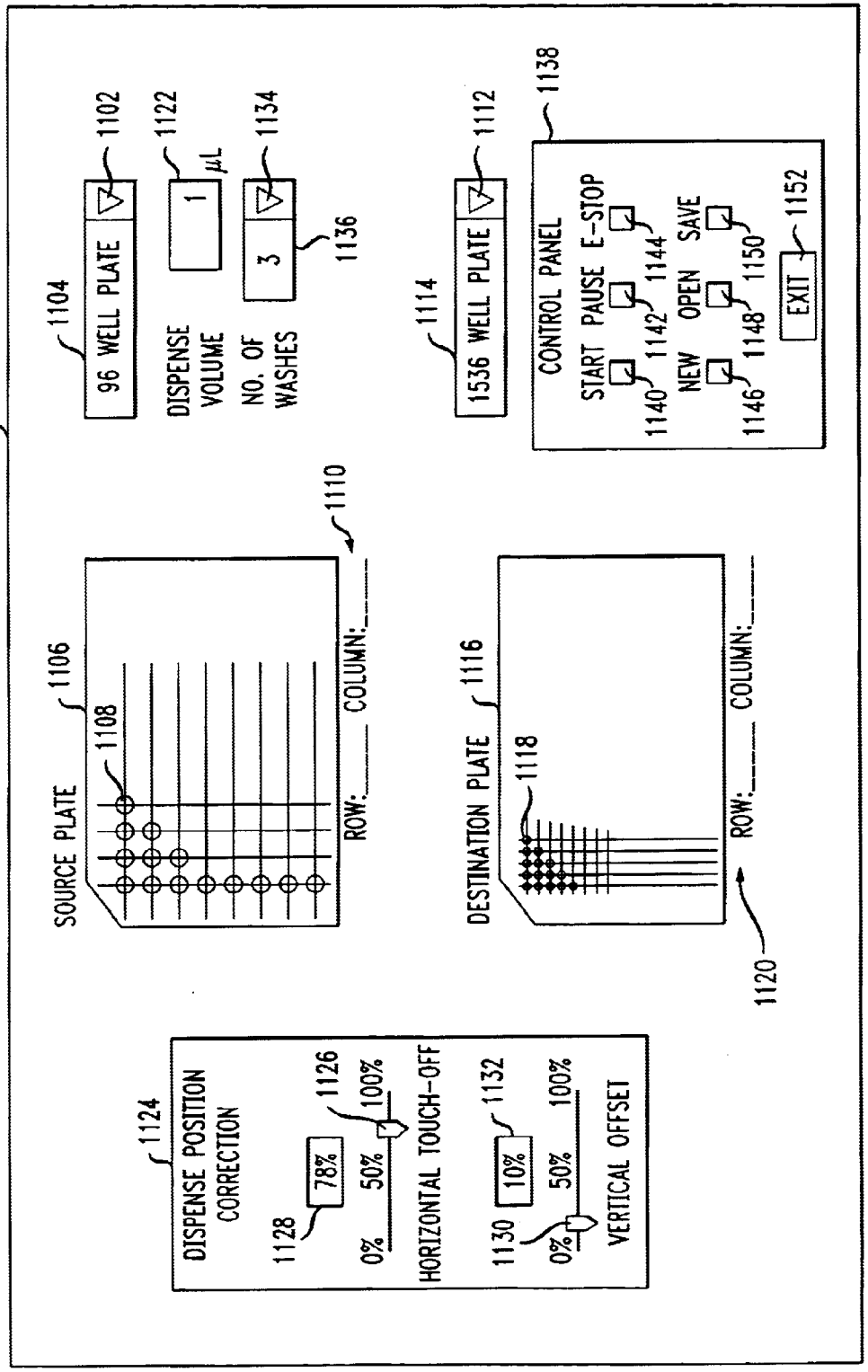
FIG. 11 depicts an illustrative graphical user interface for use in conjunction with the present single channel reformatter.
Figure 12:
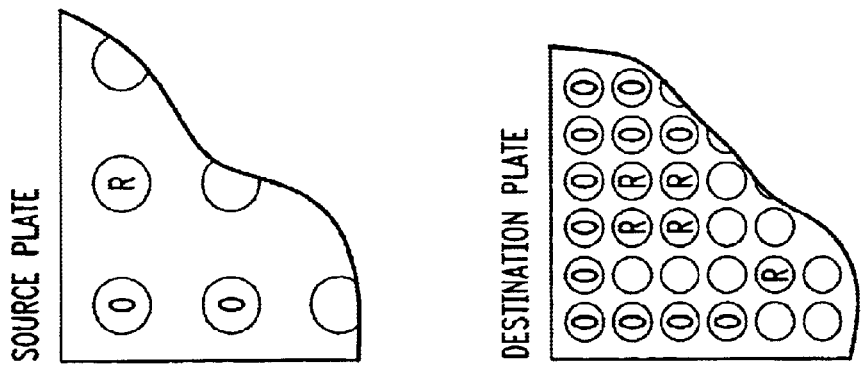
FIGS. 12 and 13 depict an illustrative methodology for tracking specified links using the graphical user interface of FIG. 11
Figure 13:
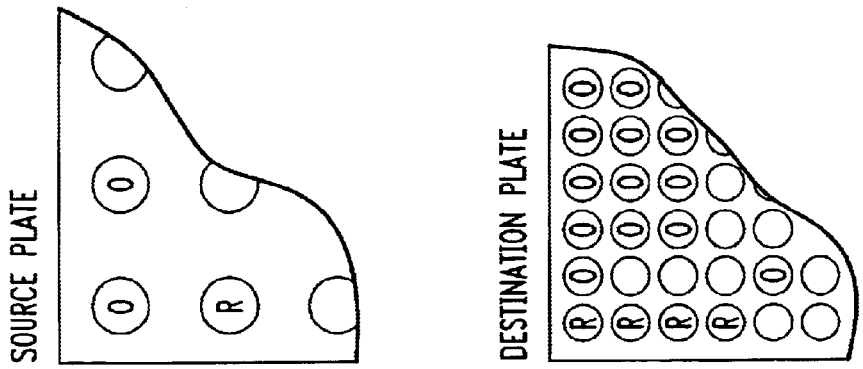
Figure 14:
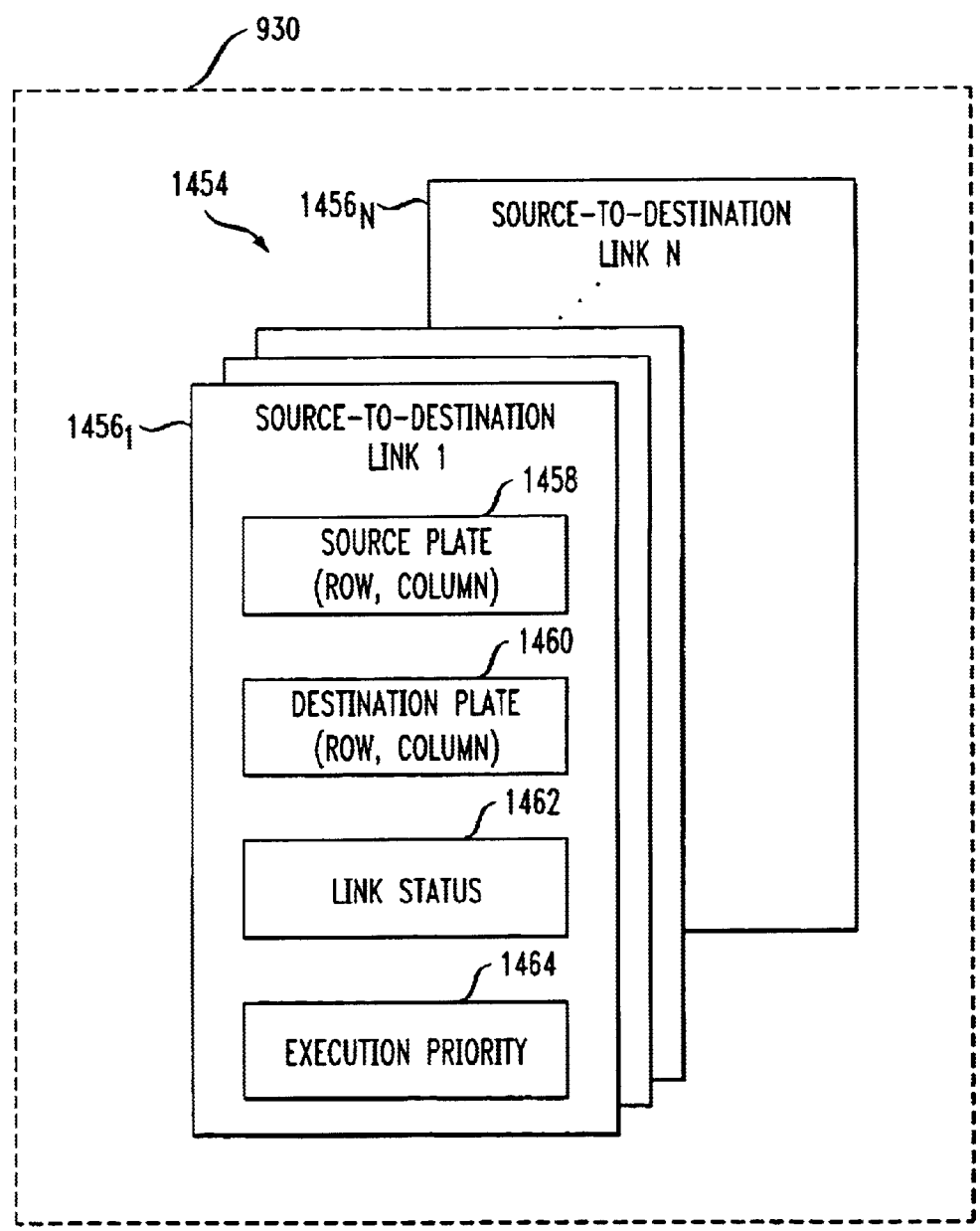
FIG. 14 depicts an illustrative data structure for organizing link data.

In accordance with operation 930 of illustrative method 900, one or more "source-to-destination links" (hereinafter "links" or "link data") that define the reformatting operations are specified. Each such link specifies a well in a source plate from which liquid is to be aspirated, and further specifies a well in a destination plate into which the aspirated liquid is to be dispensed. There are, of course, many ways in which operation 930 can be implemented via interactive software, including a variety of user interface options and, also, a variety of different data structures for organizing the link data for use by the software. FIGS. 11–13 depict an illustrative embodiment of a graphical user interface ("GUI") 1100 by which link data and other operating parameters are specified, and FIG. 14 depicts an illustrative embodiment of an array 1454 of data structures 1456$_i$ for organizing the link data within interactive software 1046.

Referring now to FIG. 11, in illustrative GUI 1100, source plate (e.g., source plate 250 of FIG. 2) is selected via icon 1102. "Clicking" on icon 1102 allows a user to select any of several format options (e.g., 96-well plate, 384 well plate, 1536 well plate, etc.). An alphanumeric description of the selected format appears in selection box 1104. Moreover, graphical representation 1106 of the selected format advantageously appears in GUI 1100. Graphical representation 1106 depicts a graphical representation 1108 of the appropriate number of wells for the selected format.

The format of the destination plate (e.g., destination plate 260 of FIG. 2) is selected via icon 1112. A description of the selected format appears in selection box 1114. Graphical representation 1116 of the destination plate, including a graphical representation 1118 of the appropriate number of wells for the selected format, advantageously appears in GUI 1100.

In some embodiments, to specify a source well, a user simply "clicks" on graphical representation 1108 of a well in the source plate. Similarly, to select a corresponding destination well, the user clicks on graphical representation 1118 of that well in the destination plate. The selected wells are advantageously "highlighted," and row-column descriptions 1110 and 1120 that identify the selected wells advantageously accompanies the graphical representations.

In other embodiments, the source and destination wells can be selected by specifying a row number and a column number in respective row-column descriptions 1110 and 1120. In such embodiments, the graphical representations 1108 and 1118 of the specified wells are advantageously highlighted to provide a pictorial description. In yet additional embodiments, the wells can be specified in both of the above-described ways.

Furthermore, rather than specifying new links in operation 930, SCR control software 1046 and GUI 1100 advantageously allow a user to recall a previously specified group of links that have been stored in memory 1044.

In some embodiments, graphical representations 1106 and 1116 of the plates keep track of selected links. In particular, in the embodiment depicted in FIG. 12, the current source well selection, which is located in the first row and second column, is highlighted by first color R (e.g., red, etc.), while previously selected source wells are highlighted in second color O (e.g., orange, etc.).

One or more destination wells may be specified for each source well. The destination wells being selected for the currently selected source well are highlighted in first color R to depict the correspondence between each destination well and the source well. Destination wells that link to previously selected source wells are highlighted by second color O. See FIG. 12. A user continues specifying links using GUI 1100 until all intended links are specified.

Link data for previously selected wells is advantageously accessed through GUI 1100. For example, in one embodiment, such data is accessed by "clicking" on a previously selected source well. As depicted in FIG. 13, accessing the previously selected source well in row 2, column 1 changes that well's highlighting from second color O to first color R. All destination wells that receive fluid from the source well are also displayed in first color R.

Returning to method 900 depicted in FIG. 9, in optional operation 932, syringe control parameters are specified, and in optional operation 934, wash system parameters are specified. Operations 932 and 934 are considered to be optional because SCR 200 could be operated with fixed values for these parameters. It is, however, advantageous to allow a user to specify such parameters.

In the embodiment depicted in FIG. 11, GUI 1100 is configured to accept syringe control parameters. The syringe control parameters included in GUI 1100 of FIG. 11 include the volume of liquid dispensed from working syringe 210 and dispense position corrections 1124. In the illustrated embodiment, syringe dispense volume is specified by inserting a number, which does not have to be an integer, in box 1122.

Regarding position corrections 1124, a user can specify the radial position of the tip of working syringe 210 within a well, wherein 0% correction corresponds to the center of the well and 100% correction corresponds to the wall or perimeter of the well. This "horizontal" position correction allows a user to create "touch-off" wherein a liquid droplet that forms at the tip of working syringe 210 contacts the wall of the well. Touch-off overcomes surface tension forces that tend to keep the droplet from disengaging from the syringe. The horizontal touch-off correction is specified by moving slider 1126 along the scale, as appropriate. The specified touch-off correction appears in box 1128.

The "vertical offset" correction specifies how deeply the syringe is positioned in a well, wherein 0% correction corresponds to the bottom of the well and 100% correction corresponds to the top of the well. This feature is particularly useful if, for example, there is another liquid already in the well, since contamination issues may arise if the syringe contacts that liquid. The vertical offset correction is specified by moving slider 1130 along the scale, as appropriate. The specified vertical offset correction appears in box 1132.

GUI 1100 of FIG. 11 is also configured to accept a wash system parameter. In particular, the user may specify the number of wash cycles that wash system 208 performs between reformatting cycles. Wash cycles are specified via icon 1134. The selected number of cycles appears in selection box 1136.

Returning to method 900 of FIG. 9, in operation 936, a preferred execution order is determined for the links that were specified in operation 930. Executing the links in the preferred order will reduce overall reformatting time relative to the time it would take to execute all such links in a random sequence. In one embodiment of a preferred execution order, links are sequenced such that:

(1) the destination well of each subsequent link is the closest well to the destination well of the previous link; and (2) irrespective of item (1), links sourced from the same source well are executed before executing a link that draws from a different source well.

For example, assume the following group of links is specified:

| Source Well (row, column) | Destination Well (row, column) |
|---|---|
| (2, 1) | (10, 15) |
| (2, 1) | (20, 30) |
| (2, 1) | (12, 25) |
| (7, 6) | (10, 16) |

In accordance with the algorithm described above, these links would be sequenced from first to last as follows:

[(2,1) (10,15)]→[(2,1) (12,25)]→[(2,1) (20,30)]→[(7,6) (10,16)].

It is within the capabilities of those skilled in the art to develop an algorithm that sequences links as described above. Moreover, it will be appreciated that other approaches for sequencing links that will likewise reduce overall execution time relative to a random execution sequence, as will occur to those skilled in the art in view of the present teachings, may suitably be used.

In the example described above, SCR control software 1046 operates such that even though more than one destination well may be receiving liquid from a single source well (assuming the transfer is to a denser format), the liquid transfer vehicle (e.g., syringe 210) returns to the source well for each transfer. In other words, even though a sufficient volume of liquid could be aspirated from the source well (e.g., source well (2,1)) to supply a multiplicity of destination wells (e.g., (10,15), (12,25), and (20,30)), a volume of liquid sufficient to supply only a single destination well is withdrawn, per aspiration, from the source well. In other embodiments, SCR control software 1046 is operative to withdraw a sufficient volume of liquid from a source well to supply multiple destination wells, as dictated by the specified links. Using such an approach in conjunction with item (1) of the sequencing algorithm further reduces reformatting time.

In operation 938, the specified links are executed. Operation 938 can be initiated using GUI 1100 by "clicking" "start" icon 1140. Start icon 1140 is advantageously grouped in control panel 1138 with a palette of other icons that are operable to initiate various functions. In the illustrated embodiment, control 1138 includes, in addition to start icon 1140, "pause" icon 1142, "e-stop" icon 1144, "new" icon 1146, "open" icon 1148, "save" icon 1150 and "exit" icon 1152. Pause icon 1142 pauses the reformatting operation at any point. E-stop icon 1144 is an emergency stop that ends the reformatting run. New icon 1146 clears source and destination plate links and allows a user to specify new links. Open icon 1148 opens a saved file of links and save icon 1150 saves a series of links. Exit icon 1152 exits the software.

In one embodiment, "execution" operation 938 includes operations 940 through 944. In operation 940, spatial coordinates for source and destination wells of links are obtained. In some embodiments, such information is contained in updateable data file 1048 (see FIG. 10). In one embodiment, the information contained in updateable data file 1048 includes, for each plate format:

(1) the absolute position of one well (typically well 1,1) with the plate disposed in the source plate receiver 456 (see FIG. 3);

(2) the absolute position of one well (typically well 1,1) with the plate disposed in the destination plate receiver 462 (see FIG. 3); and (3) the center-to-center well spacing for each format.

From this information, the spatial position of any well in a plate, with the plate in either the source position or the destination position, can be calculated in well known fashion. In another embodiment, the x-y-z coordinates of each well are stored in updateable data file 1048.

In operation 942, the spatial coordinates and other SCR control parameters (e.g., syringe control parameters and wash system control parameters, etc.) are transferred to controller 1050. Controller 1050 converts the spatial coordinates into actuator control information that drives, in operation 944, x-y positioner 201, z-positioner 206 and syringe drive 212 to aspirate liquid from the specified source wells and dispense the aspirated liquid into the specified destination wells. In terms of illustrative SCR 200 depicted in FIG. 3, the actuator control information is motor control information that drives, as appropriate, s-stepper motor 686, z-stepper motor 570, y-stepper motor 440 and x-stepper motor 1060 (not depicted in FIG. 3, see FIG. 10).

Those skilled in the art will recognize that a stepper motor driver operable to receive the motor control information from controller 1050 is required in conjunction with each stepper motor. The controller, which may be, for example, a 4-axis PC Card, is available from Acroloop Motion Control Systems of Chaska, Minn., and the stepper motor drivers are available from Applied Motion Products of Watsonville, Calif.

As will be appreciated by those skilled in the art, the various positioning systems described herein advantageously include a "home sensor" that provides a position reference to controller 1050. As depicted in FIG. 10, information from x-home sensor 1070, y-home sensor 1072, z-home sensor 1074 and s-home sensor 1076 is transmitted, via controller 1050, to processor 1042. It is within the capabilities of those skilled in the art to suitably select a home sensor and integrate it for use with any of the positioners and/or drives mentioned herein. A suitable home sensor is available from Omron of Schaumberg, Ill.

It will be appreciated that the functionality described above may be implemented in software in many different ways by those skilled in the art. For example, appreciable variation in the order in which various tasks/operations are accomplished can be expected, since the order of the operations comprising method 900 is substantially permutable. Moreover, a variety of different data structures can be developed for organizing the link data. An embodiment of one such data structure that provides certain efficiencies in terms of computer resources and processing time is described below in conjunction with FIG. 14.

To cover all possible links between wells on source plates and wells on destination plates would require an array having a maximum size of 1536×1536 (assuming a maximum plate density of 1536 wells). Thus, an array having 2.4 million data structures, each data structure containing the link data for a single link, would be required. The present inventors have substantially reduced the theoretical array size by recognizing that, notwithstanding the 2.4 million possible combinations, each well on the destination plate can link with only one well on the source plate. In other words, the link array can be reduced to a maximum of 1536 data structures, one data structure for each well on the destination plate. Such an array of data structures is depicted in FIG. 14.

Link array 1454 contains a number N of data structures 1456$_i$, where N is the number of wells in the destination plate. Each data structure 1456$_i$ contains row and column designation 1458 of a source well and row and column designation 1460 of a destination well. In some embodiments, each data structure 1456$_i$ includes link status 1462 for indicating whether the link is active (i.e., liquid is being dispensed to that particular destination well) or not, and whether the link has been executed if it is active. Additionally, in some embodiments, each data structure 1456$_i$ contains an execution priority 1464 as determined in operation 936 of method 900 (see FIG. 9).

It is to be understood that the above-described embodiments are merely illustrative of the invention and that many variations can be devised by those skilled in the art without departing from the scope of the invention. It is therefore intended that such variations be included within the scope of the following claims and their equivalents.

We claim:

1. An article comprising:
a z-positioner, wherein said z-positioner moves a liquid transfer vehicle along a z-axis but not in an x-y plane;
a x-y positioner, wherein said x-y positioner moves, in said x-y plane, a first container having a first plurality of wells and a second container having a second plurality of wells;
processing and control electronics, wherein said processing and control electronics directs said x-y positioner to align a well in said first container with said z-axis and a well in said second container with said z-axis;
a fluid control device, wherein said fluid control device generates a flow of liquid from said well of said first container into said liquid transfer vehicle and generates a flow of said liquid from said liquid transfer vehicle to said well is said second container; and
a wash system, wherein said wash system washes said liquid transfer vehicle, and wherein said wash system is coupled to said liquid transfer vehicle and said z-positioner such that z-positioning operation does not cause relative motion between said liquid transfer vehicle and said wash system.

2. A single channel reformatter comprising:
a working syringe having a first plunger, wherein said working syringe retrieves liquid from a source vessel and delivers it to a destination vessel;
a wash system comprising a first syringe and a second syringe;
a z-positioner, wherein said z-positioner is coupled to said working syringe and said wash system, and wherein said z-positioner moves said working syringe and said wash system in a z-direction with no relative movement therebetween; and
a drive mechanism, wherein said drive mechanism is mechanically coupled to said working syringe, said first syringe, and said second syringe, wherein:
movement of said drive mechanism in a first direction generates aspirating flow in said working syringe and said second syringe and dispensing flow in said first syringe; and
movement of said drive mechanism in a second direction generates dispensing flow in said working syringe and said second syringe and aspirating flow in said first syringe.

3. The article of claim 2 wherein said source vessel is a first multi-well plate having a number, m, of wells and said destination vessel is a second multi-well plate having a number, n, of wells, and wherein n is greater than m.

4. The article of claim 2 further comprising a wash/waste station, wherein said first syringe delivers cleaning fluid to said wash/waste station, and wherein said working syringe aspirates said cleaning fluid that was delivered to said wash/wash station by said first syringe.

5. The article of claim 2 further comprising a wash/waste station, wherein said working syringe dispenses contaminated cleaning fluid to said wash/waste station, and said second syringe aspirates said contaminated cleaning fluid from said wash/waste station.

6. The article of claim 2 wherein said z-positioner does not move said working syringe in an x-y plane; and further comprising an x-y positioner, wherein said x-y positioner moves said source vessel and said destination vessel in said x-y plane.

7. The article of claim 6 wherein said source vessel is a first multi-well plate having a plurality of wells and said destination vessel is a second multi-well plate having a plurality of wells; and further comprising processing and control electronics, wherein said processing and control electronics:
direct said x-y positioner to align a well in said first multi-well plate with said z-axis; and
direct said x-y positioner to align a well in said second multi-well plate with said z-axis.

8. The article of claim 7 wherein said processing and control electronics comprises interactive software through which a user specifies said well in said first multi-well plate and said well in said second multi-well plate, said interactive software including a graphical user interface that displays:
a first pictorial representation of said first multi-well plate with a first plurality of wells; and
a second pictorial representation of said second multi-well plate with a second plurality of wells;
wherein, said specified well in said first multi-well plate is identifiable in said first pictorial representation as having been specified, and said specified well in said second multi-well plate is identifiable in said second pictorial representation as having been specified.

* * * * *